United States Patent [19]

Kalvinsh et al.

[11] Patent Number: 4,686,215
[45] Date of Patent: Aug. 11, 1987

[54] PHARMACEUTICAL COMPOSITION AND METHOD FOR TREATING TUMORS SUSCEPTIBLE TO 2-CARBAMOYLAZIRIDINE

[75] Inventors: Ivars Y. Kalvinsh, Rizhsky; Elena B. Astapenok, Riga, both of U.S.S.R.

[73] Assignee: Institut Organicheskogo Sinteza Akademii Nauk SSR, Riga, U.S.S.R.

[21] Appl. No.: 693,171

[22] Filed: Jan. 22, 1985

Related U.S. Application Data

[60] Continuation of Ser. No. 581,238, Feb. 17, 1984, abandoned, which is a continuation of Ser. No. 321,933, Nov. 16, 1981, abandoned, which is a division of Ser. No. 217,253, Dec. 17, 1980, abandoned, which is a continuation of Ser. No. 844,426, Oct. 20, 1977, abandoned.

[30] Foreign Application Priority Data

Oct. 29, 1976 [SU] U.S.S.R. ................................. 2418326

[51] Int. Cl.$^4$ .............................................. A61K 31/33
[52] U.S. Cl. ..................................................... 514/183
[58] Field of Search .......................... 424/244; 514/183

[56] References Cited

PUBLICATIONS

Chemical Abstracts 59: 11424(b) (1967).
Chemical Abstracts 70: 10608(p) (1969).
Carter et al., Chemotherapy of Cancer, 2nd ed., a Wiley Medical Publication, N.Y., N.Y., 1981, pp. 26–43.

*Primary Examiner*—Jerome D. Goldberg
*Attorney, Agent, or Firm*—Burgess, Ryan & Wayne

[57] ABSTRACT

The pharmaceutical composition possessing antitumor activity against tumors susceptible to 2-carbamoylaziridine which consists of a therapeutically efficaceous quantity of 1-H-2-aziridinecarbonic acid derivative having the formula

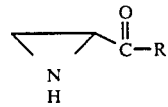

where R is $NH_2$
and a pharmaceutically suitable solvent or filler. The pharmaceutical composition possesses a high activity against tumors susceptible to 2-carbamoylaziridine, a wide spectrum of antitumor effect and low toxicity ($LD_{50}$ within the range of 3,000 and 3,500 mg/kg. The invention is also a method for treating malignant tumors susceptible to 2-carbamoxylaziridine by administration of 2-carbamoyl-aziridine.

13 Claims, No Drawings

PHARMACEUTICAL COMPOSITION AND METHOD FOR TREATING TUMORS SUSCEPTIBLE TO 2-CARBAMOYLAZIRIDINE

This is a continuation of application Ser. No. 581,238, filed Feb. 17, 1984 now abandoned which in turn is a continuation of Ser. No. 321,933 filed Nov. 16, 1981, now abandoned, which in turn is a divisional of Ser. No. 217,253, filed Dec. 17, 1980, now abandoned, which in turn is a continuation of Ser. No. 844,426, filed Oct. 20, 1977, now abandoned.

FIELD OF APPLICATION

This invention relates to pharmaceutical compositions possessing antitumor activity and, specifically, to pharmaceutical compositions comprising 2-carbamoyl aziridine as active agent and methods for treating malignant tumors susceptible to 2-carbamoylaziridine.

BACKGROUND OF INVENTION

Known in the prior art is a number of chemotherapeutic agents for treating malignant neoplasms including those which comprise aziridine derivatives as active agent, such as diaziridinyl-2-methylthiazolido-3-phosphoric acid (Imiphos), triaziridinylthiophosphoric acid (TioTef).

The pharmaceutical composition comprising 1-carbamoyl-2-cyanoaziridine is the most effective among cytostatics—agents based on aziridine derivatives intended for treating malignant neoplasms—known in the prior art.

The application of the known drugs based on the above active agents—aziridine derivatives, and specifically on 1-carbamoyl-2-cyano-aziridine, provides for 47.4% cure of rats with carcinosarcoma DS.

However, 1-carbamoyl-2-cyano-aziridine was tested only for experimental treatment (in vivo) of tumors at early stages of development and for suppression of metastases and relapse. Besides, the above compound displays rather high toxicity ($LD_{50} = 1\ 250$ mg/kg).

BRIEF DESCRIPTION OF INVENTION

An object of this invention is to provide a pharmaceutical composition based on 2-carbamoyl-aziridine with high antitumor activity against tumors susceptible to 2-carbamoylaziridine, a broad spectrum of antitumor effect and low toxicity.

In accordance with this and other objects the essence of the invention consists in a pharmaceutical composition containing a antitumor active principle against tumors susceptible to 2-carbamoylaziridine, the compound having the formula

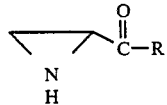

where R is $NH_2$, and also containing a pharmaceutically suitable (non-toxic) carrier, e.g. solvents or fillers. The invention also includes a method of treating malignant tumors susceptible to 2-carbamoyl-aziridine by administering to a patient suffering from said malignant tumor an anti-malignant tumor effective amount of 2-carbamoylaziridine.

The following features of the composition present considerable advantages:

(a) the composition can be used effectively at all stages of malignant growth of tumors susceptible to 2-carbamoylaziridine;

(b) the toxicity of the composition is fairly low, while the therapeutic index is considerably higher ($LD_{50}$ is within the range of 3 000 to 3 500 mg/kg).

As a pharmaceutical solvent it is recommended to use distilled water or isotonic solution.

When combining the active principle with a pharmaceutical solvent it is recommended to use a pharmaceutical composition comprising the active principle in the amount of 0.1–30% (by weight).

It is recommended to select a pharmaceutical filler from a group consisting of stearic acid, lactose, glucose, potato starch, talc, vegetable oils, polyethyleneglycol taken separately or in different combinations. When the active principle is combined with a pharmaceutical filler for tablets and dragees it is recommended to use a pharmaceutical composition with active principle content 10–55% (by weight).

When the active principle is combined with a pharmaceutical filler for suppositories it is recommended to use a pharmaceutical composition with the active principle content 1–50% (by weight).

When the active principle is combined with a pharmaceutical filler for ointment it is recommended to use a composition with the active principle content 0.1–50% (by weight).

DETAILED DESCRIPTION OF INVENTION

The active principle—1-H-2-aziridinecarbonic acid derivative of the above formula where R is $NHNH_2$ can be obtained as follows.

1.5 ml of anhydrous hydrazine are added dropwise under cooling and intensive stirring to 5.05 g (0.05 mol) of methyl ester of aziridine-2-carbonic acid at such speed that the temperature of the mixture should not exceed $+10°$ C. The reaction mixture is stirred during 10 minutes, and 50 ml of ethyl ether are added thereto. The colorless residue is filtered off and dried under reduced atmospheric pressure. Yield 4.04 g (80%), melting point 120° C. (with decomposition).

After crystallization with activated carbon from acetonitrile the melting point of the substance is 122°–124° C. (with decomposition). PMR spectrum in $D_2O$, $\tau$, ppm: 7.41 ($C^1H$), 8.03 ($C^2H$), 8.12 ($C^2H$). Constants of spin-spin interaction: $J^{gem}=0.8$ Hz, $J_{trans}^{vic}=3.3$ Hz, $J_{cis}^{vic}=5.8$ Hz. IR-spectrum, $cm^{-1}$: 1680 (C=O), 1620, 3180, 3240, 3330 ($NH + NHNH_2$).

Found, %: C 35.8; H 7.2; N 41.6. $C_3H_7N_3O$. Calculated, %: C 35.6; H 6.9; N 41.5.

The active principle 2-carbamoylziridine can be obtained as follows.

10.1 g (0.1 mol) of methyl ester of 1-H-2-aziridinecarbonic acid were dissolved in 35 ml of methanol and were saturated with anhydrous ammonia during 24 hours. After the suspension cooled, colorless crystals were filtered off and crystallized from absolute ethanol to obtain 7.3 g (84%) of 1-H-2-aziridinecarbonic acid amide with the melting point 117°–119° C. which were dissolved in ethyl alcohol, treated with silica gel and activated carbon, and then evaporated. After recrystallization from absolute ethanol the melting point is 132°–134° C. PMR spectrum in DMSO-$d_6$, $\tau$, ppm: 7.64 (CH), 8.37 ($CH_2$), 9.5 (NH), 2.3 and 2.8 ($NH_2$).

Found, %: C 41.7; H 6.6; N 36.2.$C_3H_6N_2O$. Calculated, %: C 41.8; H 6.8; N 36.4.

The processes according to the present invention have an advantage of simple process technology and isolation of the desired products with a good yield.

The pharmaceutical composition of the present invention displayed high activity at all stages of tumor development in experiments in vivo in rats bearing SA-45 which opens up a new perspective in treating malignant neoplasms. Non-linear male rats with the starting weight 120-150 g were used in the experiments described hereinunder in Examples 1-4. All the animals were administered intravenously a single dose of the pharmaceutical composition in the form of the concentrated solution (10-30%) of the active principle in distilled water at a rate of 1500 mg/kg. The animals were decapitated on the 20th say from the day of the administration. All the animals received the usual laboratory ration.

EXAMPLE 1

The action of the pharmaceutical composition consisting of 30% solution of the active principle of the above formula where R is $NHNH_2$, in distilled water on tumor growth was tested in rats with implanted mammary gland cancer (RMGC-1). The results of the experiments are presented in Table 1, where I—control animals, II—rats which were administered the pharmaceutical composition, III—rats which were administered the same composition against the background of 90 minutes' hyperglycemia. The animals of groups II and III were administered the composition 24 hours after tumor implantation.

TABLE 1

| Group | Number of animals | Complete disappearance of the tumor | Partial disappearance of the tumor | No effect |
|---|---|---|---|---|
| I | 10 | — | — | 10* |
| II | 10 | 8 | — | 2 |
| III | 10 | 7 | 2 | 1 |

*70% of the controls survived till the day of decapitation. The average weight of the tumor by the end of the experiment was 25-30 g.

EXAMPLE 2

The action of the same pharmaceutical composition as in Example 1 was tested in rats with implanted RMCC-1 at late stage of tumor development. The pharmaceutical composition was administered 15 days after tumor implanatation, the average weight of the tumor being 35 g. The groups of the animals are designated as in Example 1. The results of the experiment are shown in Table 2. None of the controls survived till the day of decapitation (the 20th day after the administration of the pharmaceutical composition to group II).

TABLE 2

| Group | Number of animals | Complete disappearance of the tumor | Partial disappearance of the tumor | No effect |
|---|---|---|---|---|
| I | 6 | — | — | 6 |
| II | 6 | 3 | 3* | — |

*Life time increased by 50%.

EXAMPLE 3

The action of the same pharmaceutical composition as in Example 1 was tested in rats with implanted SA-45 at early stages of tumor development. The pharmaceutical composition was administered 48 hours after tumor implantation. The results of the experiment are presented in Table 3, where I—control group, II—rats which were administered pharmaceutical composition.

TABLE 3

| Group | Number of animals | Complete disappearance of the tumor | Partial disappearance of the tumor | No effect |
|---|---|---|---|---|
| I | 10 | — | — | 10 |
| II | 10 | 3 | 3 | 4 |

EXAMPLE 4

The action of the pharmaceutical composition consisting of 30% solution of the active principle above formula where R is $NH_2$, in distilled water was tested in rats with SA-45 at late stages of tumor development. The composition was administered 17 days after tumor implantation. The results of the experiment are presented in Table 4 where I—control animals, II—rats which were administered the pharmaceutical composition.

TABLE 4

| Group | Number of animals | Complete disappearance of the tumor | Partial disappearance of the tumor | No effect |
|---|---|---|---|---|
| I | 10 | — | — | 10 |
| II | 10 | 6 | 2 | 2 |

Since the active principle of the above general formula is easily soluble in water, concentrated aqueous solutions of the mentioned active principle can be used effectively for treating humans.

It is preferable to administer the pharmaceutical composition intravenously (dropwise) at a single dose of 150-250 mg/kg. The dose may vary from 50 to 500 mg/kg of the active principle, the given amount may be divided for 2-4-fold administration.

Apart from distilled water isotonic solution can be used as a solvent. The active principle can be also used in combination with pharmaceutically suitable (non-toxic) filler(s) for peroral administration in the form of tablets, dragee or capsules, or application in the form of suppositories or ointment.

When the pharmaceutical composition is used in the form of injection solutions the active principle is produced in the form of sterile, for instance, modified powder, and the pharmaceutical solvent is stored in ampules. The pharmaceutical composition in the form of hermetically sealed tablets, dragee and capsules can be stored not less than for a year, and in the form of suppositories and ointment at 0-(+4)°C.— not less than for 6 months, its activity being preserved.

The use of the described active principle in the pharmaceutical composition of this invention having antimalignant tumor activity is bound to open new perspectives in combating malignant tumors which are susceptible to 2-carbamoylaziridine as compared with the cytostatics in the prior art.

We claim:

1. Method of treating a malignant tumor susceptible to 2-carbamoylaziridine, which comprises administering to a patient suffering from said malignant tumor, an anti-malignant tumor effective amount of 2-carbamoylaziridine.

2. Method according to claim 1 wherein said administration is by injection.

3. Method according to claim 1 wherein said administration is peoral.

4. Method according to claim 1 wherein said administration is by suppository.

5. A pharmaceutical composition possessing antitumor activity against malignant tumors susceptible to 2-carbamoylaziridine and being adapted for administration to humans to effect said anti-malignant tumor activity, said composition comprising an anti-malignant tumor effective amount of 2-carbamoylaziridine and a pharmaceutically acceptable sterile solvent.

6. The pharmaceutical composition of claim 5 wherein distilled water is used as the solvent.

7. The pharmaceutical composition of claim 5 wherein isotonic solution is used as the solvent.

8. The pharmaceutical composition of claim 5 wherein the content of said 2-carbamoylaziridine in the composition is 0.1–30% by weight.

9. A pharmaceutical composition possessing antitumor activity against malignant tumors susceptible to 2-carbamoylaziridine and being in the form of tablets, dragees capsules, suppositories or ointments for administration to humans to effect said anti-malignant activity, said composition comprising an anti-malignant tumor effective amount of 2-carbamoylaziridine and a pharmaceutically acceptable filler.

10. The pharmaceutical composition of claim 9 wherein said pharmaceutical filler is selected from the group consisting of stearic acid, lactose, glucose, potato starch, talc, vegetable oils, and polyethyleneglycol.

11. The pharmaceutical composition of claim 9 in the form of tablets or dragees and wherein the content of said 2-carbamoylaziridine in the composition is 10–55% by weight.

12. The pharmaceutical composition of claim 9 in the form of suppositories and wherein the content of said 2-carbamoylaziridine composition is 1–50% by weight.

13. The pharmaceutical composition of claim 9 in ointment form and wherein the content of said 2-carbomoylaziridine in the composition is 0.1–50% by weight.

* * * * *